US011400205B2

(12) United States Patent
Van Niekerk et al.

(10) Patent No.: US 11,400,205 B2
(45) Date of Patent: Aug. 2, 2022

(54) BALLOON-IN-BALLOON IRRIGATION BALLOON CATHETER

(71) Applicant: Biosense Webster (Israel) Ltd., Yokneam (IL)

(72) Inventors: Pieter Emmelius Van Niekerk, Monrovia, CA (US); Cesar Fuentes-Ortega, Pasadena, CA (US); Erik Lazo, Yokneam (IL); Jace P. Valls, Pasadena, CA (US); Kevin Justin Herrera, Irvine, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 241 days.

(21) Appl. No.: 16/731,333

(22) Filed: Dec. 31, 2019

(65) Prior Publication Data

US 2020/0147295 A1 May 14, 2020

Related U.S. Application Data

(63) Continuation-in-part of application No. 15/360,967, filed on Nov. 23, 2016, now Pat. No. 10,821,272.

(51) Int. Cl.
*A61B 18/14* (2006.01)
*A61M 3/02* (2006.01)
*A61M 25/10* (2013.01)
*A61B 6/00* (2006.01)
*A61B 18/00* (2006.01)

(52) U.S. Cl.
CPC ....... *A61M 3/0295* (2013.01); *A61B 18/1492* (2013.01); *A61M 3/0258* (2013.01); *A61M 25/1011* (2013.01); *A61M 25/10181* (2013.11); *A61B 6/485* (2013.01); *A61B 2018/00029* (2013.01); *A61B 2018/00351* (2013.01); *A61B 2018/00577* (2013.01); *A61M 2025/1013* (2013.01); *A61M 2025/1086* (2013.01); *A61M 2205/3334* (2013.01); *A61M 2205/3344* (2013.01); *A61M 2205/3368* (2013.01); *A61M 2205/50* (2013.01); *A61M 2210/125* (2013.01)

(58) Field of Classification Search
CPC ..... A61B 18/14; A61B 18/1492; A61B 18/02; A61B 18/04
See application file for complete search history.

(56) References Cited

U.S. PATENT DOCUMENTS

| 5,391,199 A | 2/1995 | Ben-Haim |
| 5,443,489 A | 8/1995 | Ben-Haim |
| 5,558,091 A | 9/1996 | Acker et al. |

(Continued)

FOREIGN PATENT DOCUMENTS

| EP | 2 076 308 B1 | 2/2013 |
| EP | 2 875 790 A2 | 5/2015 |
| EP | 3 326 563 A1 | 5/2018 |

OTHER PUBLICATIONS

Extended European Search Report for European Application No. EP17203142, dated Apr. 4, 2018, 10 pages cited in parent application (U.S. Appl. No. 15/360,967).

*Primary Examiner* — Jon Eric C Morales
(74) *Attorney, Agent, or Firm* — Troutman Pepper Hamilton Sanders LLP

(57) ABSTRACT

An irrigation balloon catheter includes one or more inner balloons inside of an irrigation balloon. The inner balloon(s) can be compliant with a volume that is dynamically adjustable for rapid inflation, rapid deflation, complete deflation, and/or irrigation flow adjustment.

20 Claims, 10 Drawing Sheets

(56) References Cited

U.S. PATENT DOCUMENTS

| | | |
|---|---|---|
| 5,814,016 A | 9/1998 | Valley |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,456,864 B1 | 9/2002 | Swanson et al. |
| 6,491,711 B1 | 12/2002 | Durcan |
| 6,690,963 B2 | 2/2004 | Ben-Haim et al. |
| 6,788,967 B2 | 9/2004 | Ben-Haim et al. |
| 7,727,228 B2 | 6/2010 | Abboud et al. |
| 9,033,965 B2 | 5/2015 | Ingle et al. |
| 9,907,610 B2 | 3/2018 | Beeckler et al. |
| 2014/0358137 A1 | 12/2014 | Hu |
| 2016/0317221 A1 | 11/2016 | Roiux |
| 2018/0140807 A1 | 5/2018 | Herrera et al. |
| 2019/0298441 A1 | 10/2019 | Clark et al. |

BALLOON-IN-BALLOON IRRIGATION BALLOON CATHETER

PRIORITY

This application claims the benefit of priority as a continuation-in-part to U.S. patent application Ser. No. 15/360,967 now US Patent Application Publication US 2018/0140807, which prior patent application is hereby incorporated by reference as if set forth in full herein.

BACKGROUND

A variety of medical treatments utilize a variety of catheters to provide fluids intravascularly to patients. In some treatments, it can be advantageous to deliver such fluids through an irrigation balloon catheter. For example, U.S. Pat. No. 9,907,610, U.S. Patent Publication 2018/0140807 and U.S. Patent Publication 2019/0298441, each hereby incorporated by reference herein as if set forth in their entirety and attached as an appendix hereto, disclose procedures utilizing an irrigation balloon catheter to provide fluid for controlling temperature of blood and/or tissue during ablation of heart tissue.

SUMMARY

An example irrigation balloon catheter can include a tubular body, an irrigation balloon, an inner balloon, an irrigation lumen, and an inflation lumen. The irrigation balloon catheter is configured such that deflation of the inner balloon causes a rapid deflation of the irrigation balloon.

The tubular body can be sized to traverse vasculature of a patient.

The irrigation balloon can include pores therethrough. The irrigation balloon can be inflatable to have a first inflated shape that is circularly symmetrical about a longitudinal axis when the irrigation balloon is unconstrained.

The inner balloon is positioned within the irrigation balloon. The inner balloon can be inflatable to have a second inflated shape that is circularly symmetrical about the longitudinal axis and separated from the first inflated shape of the irrigation balloon at least in the vicinity of the pores. Alternatively, the inner balloon can be inflatable to have a second inflated shape that includes longitudinal indented ridges aligned with the pores of the irrigation balloon such that the outer surface of the inner balloon in the second inflated shape in the vicinity of the ridges is a further distance from the inner surface irrigation balloon in the first shape compared a distance between the inner surface of the irrigation balloon in the first shape and outer surfaces, away from the vicinity of the ridges, of the inner balloon in the second shape.

The irrigation lumen is in communication with the irrigation balloon and extends along the tubular body. The inflation lumen is in communication with the inner balloon and extends along the tubular body. The irrigation lumen and inflation lumen can be isolated from each other.

The irrigation balloon can be affixed to the inner balloon at first and second balloon ends. The first inflated shape can be circularly symmetrical about the longitudinal axis from the first balloon end to the second balloon end. The second inflated shape can be circularly symmetrical about the longitudinal axis from the first balloon end to the second balloon end. Alternatively, the second inflated shape of the inner balloon can include a petal-shaped cross sectional shape when the inner balloon includes indented ridges.

The pores of the irrigation balloon can define one or more planes perpendicular to the longitudinal axis. The second inflated shape of the inner balloon can include a circular cross section in each of the one or more planes. Alternatively, the second inflated shape of the inner balloon can include a petal-shaped cross sectional shape when the inner balloon includes indented ridges.

The irrigation balloon can include a non-compliant membrane. The inner balloon can include a compliant or semi-compliant membrane.

The pores can be sized to allow saline solution to pass therethrough.

The second inflated shape can include a volume that of about 70% to about 90% of a volume of the first inflated shape.

The inner balloon can include a fluid impermeable membrane.

An example system can include an irrigation balloon catheter, a continuous flow pump, and an inflator tool. The system can further include a processor and computer readable medium in communication with the processor. The irrigation balloon catheter can include a tubular body, an irrigation balloon, an inner balloon, an irrigation lumen, and an inflation lumen.

The tubular body can be sized to traverse vasculature of a patient.

The irrigation balloon can include pores therethrough. The irrigation balloon can be inflatable to have a first inflated shape that is circularly symmetrical about a longitudinal axis when the irrigation balloon is unconstrained.

The inner balloon is positioned within the irrigation balloon. The inner balloon can be inflatable to have a second inflated shape that is circularly symmetrical about the longitudinal axis and separated from the first inflated shape of the irrigation balloon at least in the vicinity of the pores. Alternatively, the inner balloon can be inflatable to have a second inflated shape that includes longitudinal indented ridges aligned with the pores of the irrigation balloon such that the outer surface of the inner balloon in the second inflated shape in the vicinity of the ridges is a further distance from the inner surface irrigation balloon in the first shape compared a distance between the inner surface of the irrigation balloon in the first shape and outer surfaces, away from the vicinity of the ridges, of the inner balloon in the second shape.

The irrigation lumen can be in communication with the irrigation balloon and extend along the tubular body, and The inflation lumen can be in communication with the inner balloon and extend along the tubular body.

The continuous flow pump can be in communication with the irrigation balloon via the irrigation lumen.

The inflator tool can be in communication with the inner balloon via the inflation lumen.

The computer readable medium can include instructions thereon that when executed by the processor cause the processor to: provide a command signal to the inflator tool to cause the inflator tool to provide a first fluid at a predetermined pressure; and provide a command signal to the continuous flow pump to cause the continuous flow pump to pump a second fluid at a predetermined flow rate. The computer readable medium can further include instructions thereon that when executed by the processor cause the processor to: receive a feedback signal from the continuous flow pump; and provide, in response to receiving the feedback signal, a command signal to the inflator tool to cause the inflator tool to decrease pressure of the first fluid.

The irrigation balloon catheter can further include one or more thermocouples disposed on the irrigation balloon. The computer readable medium can further include instructions thereon that when executed by the processor cause the processor to: receive one or more signals from the one or more thermocouples; and provide, in response to receiving the one or more signals from the one or more thermocouples, a command signal to the inflator tool to cause the inflator tool to decrease pressure of the first fluid.

An example method of treatment can include one or more of the following steps presented in no particular order. An irrigation balloon catheter including an inner balloon and irrigation balloon can be traversed through vasculature of patient. The inner balloon can be inflated inside of the irrigation balloon. Irrigation fluid can be flowed through a volume defined by an inner surface of the irrigation balloon and an outer surface of the inner balloon and through pores of the irrigation balloon. Flow of the irrigation fluid through one or more of the pores of the irrigation balloon can be adjusted by resizing the inner balloon.

The method can further include expelling irrigation fluid from the volume defined by the inner surface of the irrigation balloon and the outer surface of the inner balloon by increasing the volume of the inner balloon.

The method can further include deflating the inner balloon immediately after expelling irrigation fluid from the volume defined by the inner surface of the irrigation balloon and the outer surface of the inner balloon.

The method can further include detecting blockage of some or all of the one or more pores. The volume of the inner balloon can be decreased in response to detecting blockage of some or all of the one or more pores.

The method can further include decreasing the volume of the inner balloon while flowing irrigation fluid through the volume defined by the inner surface of the irrigation balloon and the outer surface of the inner balloon and through pores of the irrigation balloon so that the irrigation balloon can be rapidly deflated by the rapid decrease in the volume of the inner balloon.

The method can further include decreasing the volume of the irrigation balloon solely by decreasing the volume of the inner balloon.

Another example method of treatment can include one or more of the following steps presented in no particular order. An irrigation balloon catheter including an inner balloon and irrigation balloon can be traversed through vasculature of patient. The inner balloon can be inflated inside of the irrigation balloon. Irrigation fluid can be flowed through a volume defined by an inner surface of the irrigation balloon and an outer surface of the inner balloon and through pores of the irrigation balloon. Irrigation fluid can be expelled from the volume defined by the inner surface of the irrigation balloon and the outer surface of the inner balloon by increasing the volume of the inner balloon The method can further include deflating the inner balloon immediately after expelling irrigation fluid from the volume defined by the inner surface of the irrigation balloon and the outer surface of the inner balloon.

Another example irrigation balloon catheter can include a tubular body, an irrigation balloon, an inner balloon, an irrigation lumen, and an inflation lumen. The tubular body can be sized to traverse vasculature of a patient. The irrigation balloon can have pores therethrough. The irrigation balloon can be inflatable to a first inflated shape that is circularly symmetrical about a longitudinal axis when the irrigation balloon is unconstrained. The inner balloon can be positioned within the irrigation balloon. The inner balloon can be inflatable to comprise a second inflated shape comprising longitudinal ridges aligned with the pores of the irrigation balloon and separating the outer surface of the inner balloon from the inner surface of the outer balloon in the vicinity of the pores. The irrigation lumen can be in communication with the irrigation balloon and extend along the tubular body. The inflation lumen can be in communication with the inner balloon and extend along the tubular body so that deflation of the inner balloon causes a rapid deflation of the irrigation balloon.

Another example irrigation balloon catheter can include a tubular body, an irrigation balloon, multiple inner balloons, an irrigation lumen, and multiple inflation lumens. The tubular body can be sized to traverse vasculature of a patient. The irrigation balloon can have pores therethrough. The inner balloons can each be inflatable within the irrigation balloon. The irrigation lumen can be in communication with the irrigation balloon and extend along the tubular body. The inflation lumens can each be in communication with a respective inner balloon of the plurality of inner balloons and extend along the tubular body.

DETAILED DESCRIPTION

Figure 1:
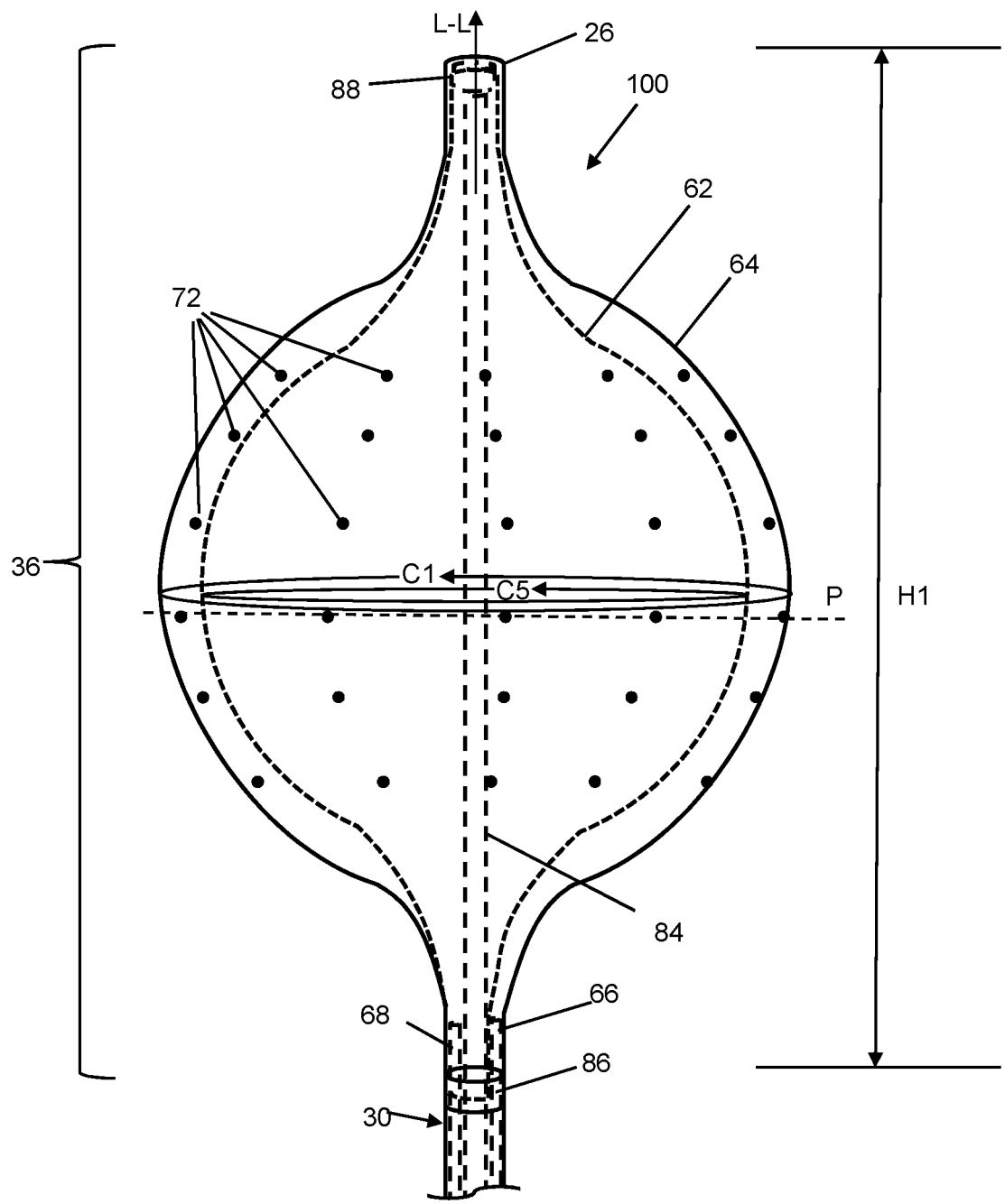
FIG. 1 is an illustration of a distal portion of a balloon-in-balloon irrigation balloon catheter in an inflated state according to aspects of the present invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%.

As used herein, the terms "patient," "host," "user," and "subject" refer to any human or animal subject and are not intended to limit the systems or methods to human use, although use of the subject invention in a human patient represents a preferred embodiment.

As used herein, the term "computing system" is intended to include stand-alone machines or devices and/or a combination of machines, components, modules, systems, servers, processors, memory, sensors, detectors, user interfaces, computing device interfaces, network interfaces, hardware elements, software elements, firmware elements, and other computer-related units. By way of example, but not limitation, a computing system can include one or more of a general-purpose computer, a special-purpose computer, a processor, a portable electronic device, a portable electronic medical instrument, a stationary or semi-stationary electronic medical instrument, or other electronic data processing apparatus.

As used herein, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal. Computer readable medium can be non-transitory. Non-transitory computer-readable media include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable instructions and/or data.

As used herein, the terms "tubular" and "tube" are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered outer surface, a curved outer surface, and/or a partially flat outer surface without departing from the scope of the present disclosure.

Figure 2:
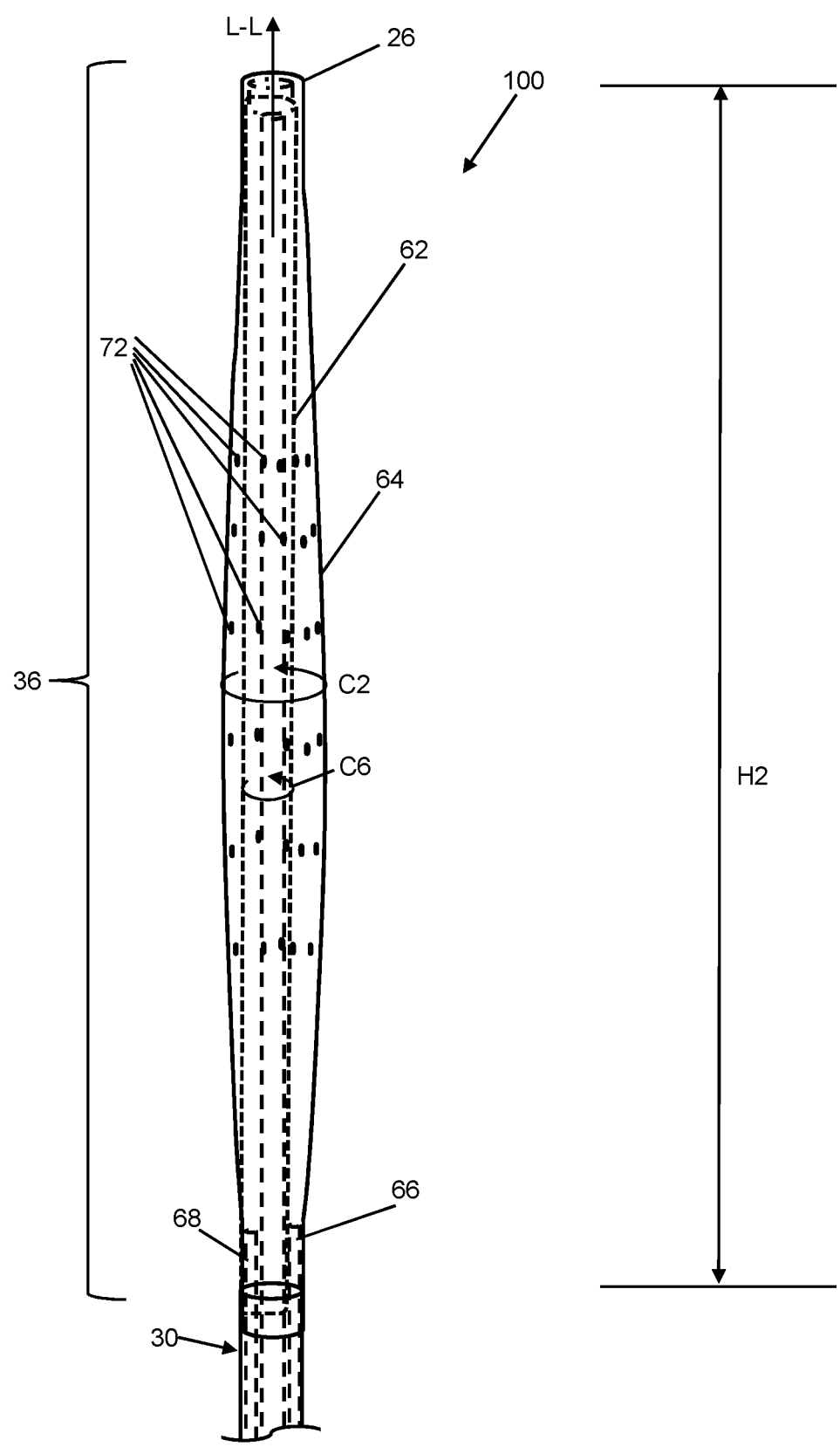
FIG. 2 is an illustration of a distal portion of a balloon-in-balloon irrigation balloon catheter in an uninflated state according to aspects of the present invention.
Figure 3:
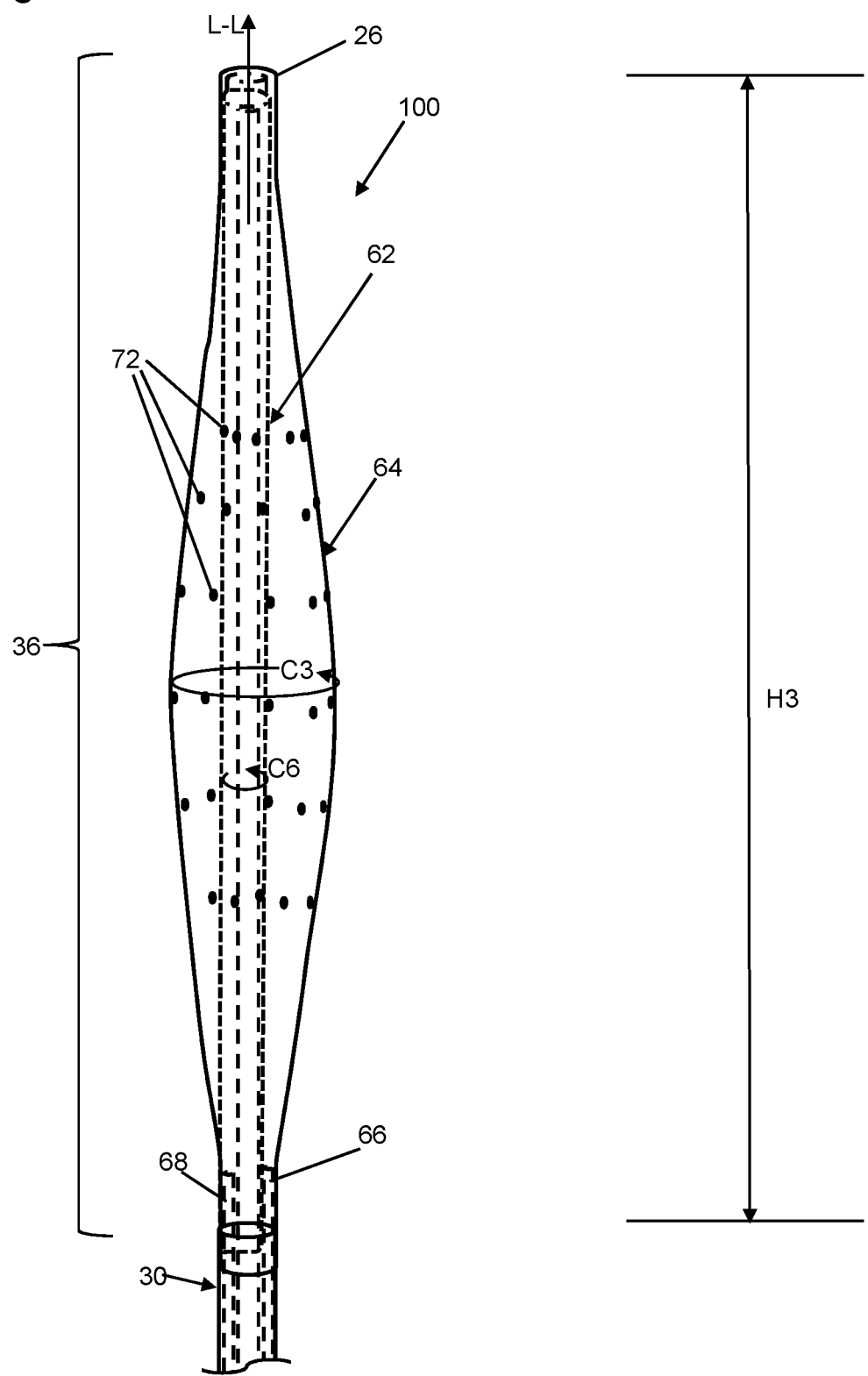
FIG. 3 is an illustration of a distal portion of a balloon-in-balloon irrigation balloon catheter in a deflated state according to aspects of the present invention.

FIGS. 1-3 illustrate a distal portion 36 of a balloon-in-balloon irrigation balloon catheter 100, where the catheter 100 is illustrated in an inflated state in FIG. 1, in an uninflated state in FIG. 2, and in a deflated state in FIG. 3. When uninflated (FIG. 2), the catheter 100 is sized and otherwise configured to traverse vasculature of a patient so that the distal portion 36 can be positioned at treatment areas in or adjacent to the heart. Once positioned at a treatment site, the catheter 100 can be inflated (FIG. 1). Following treatment, the catheter 100 can be deflated (FIG. 3) for repositioning or extraction.

Referring collectively to FIGS. 1-3, as illustrated, the catheter 100 includes an irrigation balloon 64 near the distal end 26 of the catheter 100, an irrigation lumen 66 providing a conduit for irrigation fluid to the irrigation balloon 64, an inner balloon 62 inside of the irrigation balloon 64, and an inflation lumen 68 providing a conduit for fluid to inflate the inner balloon 62. The irrigation balloon 64 and inner balloon 62 are affixed to each other at a distal balloon end 88 and a proximal balloon end 86. The irrigating balloon 64 includes pores 72 sized and positioned to allow irrigation fluid to exit the interior of the irrigation balloon 64. The non-irrigating inner balloon 62 is impermeable to the irrigation fluid such that no significant amount of irrigation fluid passes from the outer balloon 64 into the inner balloon 62 when negative pressure is applied to deflate the inner balloon 62, meaning any amount of irrigation fluid that may enter the inner balloon 62 during deflation does not significantly affect the resulting volume of the inner balloon. The irrigation lumen 66 and inflation lumen 68 are positioned in an insertion tube 30. The insertion tube 30, irrigation lumen 66, and inflation lumen 68 can have sufficient length to extend from the treatment site, through vasculature, and outside the patient. The distal portion 36 of the catheter 100 can be placed by manipulation of a proximal portion of the insertion tube 30. Fluids can be injected into respective proximal openings of the irrigation lumen 66 and inflation lumen 68.

Configured as such, the volume of the inner balloon 62 can be deflated more rapidly than an equivalent volume of an irrigation balloon lacking the inner balloon structure 62. This is because, generally, an irrigation balloon includes pores that allow backflow of fluids into the volume of the irrigating balloon when negative pressure is applied to deflate the irrigating balloon.

The inner balloon 62 can also provide a greater degree of deflation of the irrigation balloon 64 compared to an irrigation balloon lacking the inner balloon structure 62. In other words, the inner balloon 62 acts as a vacuum pump to the irrigation balloon 64 to cause rapid deflation (i.e., a rate of deflation with the inner balloon 62 as compared to a rate of deflation without the inner balloon). Generally, an irrigation balloon lacking an inner balloon structure 62 may not sufficiently deflate for safe traversal of vasculature by negative pressure alone due to the pores. One strategy for addressing insufficient deflation involves pulling the irrigation balloon into a sheath, causing the irrigation balloon to compress and thereby expel fluid through the pores. In such instances, force between the end of the sheath and the outside of the irrigation balloon may lead to peeling of surfaces features of the irrigation balloon, rupture of the irrigation balloon, or other damage to the surface of the irrigation balloon.

Referring to FIG. 1, in the inflated configuration, the irrigation balloon 64 and inner balloon 62 can each be substantially circularly symmetrical about a longitudinal axis L-L. The inner balloon 62 is illustrated as being separated from the irrigation balloon 64 at least in the vicinity of the pores 72 to allow irrigation fluids to pass from the irrigation lumen 66, between the outer surface of the inner balloon 62 and the inner surface of the irrigation balloon 64, and out of the pores 72. The irrigation balloon 64 can be substantially circularly symmetrical about the longitudinal axis L-L from the proximal balloon end 86 to the distal balloon end 88. The inner balloon 62 can be substantially circularly symmetrical about the longitudinal axis L-L from the proximal balloon end 86 to the distal balloon end 88. The balloons 62, 64 can be substantially circularly symmetrical about the longitudinal axis L-L between the balloon ends 86, 88 but not perfectly symmetrical near the proximal balloon end 86 due to the positioning of the irrigation lumen 66 and inflation lumen 68. The pores 72 in the irrigation balloon 64 can define one or more planes P that are perpendicular to the longitudinal axis L-L. The inner balloon 62 and irrigation balloon 64 can each have a circular cross section in some or all of the perpendicular planes P defined by the pores 72. Further, in one or more of the perpendicular planes P, the circular cross section of the inner balloon 62 and irrigation balloon 64 can be concentric. Being circularly symmetrical, volume of the inner balloon 62, irrigation balloon 64, and space between the two balloons 62, 64 are each a function of the circumference of the balloons 62, 64 as appreciated and understood by a person of ordinary skill in the art. The inner balloon 62, when inflated, constitutes a percentage of the internal volume of the outer balloon 64. The percentage of inflation can be controlled during a procedure if the inner and/or outer balloon is compliant, or the percentage can be controlled by the shape and size of the balloons if both balloons are non-compliant. In either case, the greater the percentage of volume that the inner balloon 62 constitutes within the outer balloon, the more rapidly the balloon pair can be inflated. In some applications, the inner balloon 62, when inflated, preferably constitutes approximately 70% to approximately 90% of the volume of the inflated outer irrigation balloon 64.

Referring collectively to FIGS. 1 through 3, the inner balloon 62 can be configured to be inflated and deflated using an inflator tool. The outer balloon 64 can be configured to be inflated then maintained at a desired flow rate and/or pressure using a continuous flow pump. The catheter 100 can be configured to allow an operator to deflate the balloons 62, 64 to allow for repositioning or removal of the catheter 100 by slightly reducing fluid flow to the outer irrigating balloon 64 and then rapidly deflating the inner balloon 62 using the deflater tool. Absent significant flow to the irrigation balloon 64, deflation of the inner balloon 62 can cause the irrigation balloon 64 to collapse to a size that can be retracted through vasculature, meaning further strategies to deflate the irrigation balloon 64 (e.g. wringing out the irrigation balloon by pulling into a sheath) are not necessary to reduce the size to the irrigation balloon 64.

The inner balloon 62 can further be non-irrigating such that the inner balloon 62 is impermeable to fluids used to inflate the inner balloon, although such function is not necessarily required to achieve rapid deflation or greater degree of deflation of the irrigation balloon 64 compared to an irrigation balloon lacking the inner balloon structure 62. In some examples, the inner balloon 62 can be suitable to be inflated by a fluoroscopic fluid, water, saline, and/or air. In some applications, the fluid for inflation of the inner balloon 62 can include a fluoroscopic or other contrast agent to aid in visualization of the distal portion of the catheter 100 within a patient. In such applications, it can be advantageous for the inner balloon 62 to be a non-irrigating balloon to confine the contrast agent to the inner balloon 62.

In some examples, the inner balloon 62 can include an elastic material such as silicone tubing or another polymer that is able to stretch while also having the ability to relax to its original (i.e., extended and non-inflated) tubular shape. The outer balloon 64 can include materials such as Pellethane® produced by the Lubrizol Corporation (Wickliffe, Ohio, U.S.A.), polyurethane, Pebax® produced by Arkema S.A. (Colombes, France), nylon, polyethylene terephthalate (PET), or a blend or combination of these materials. The inner balloon 62 is preferably more compliant than outer balloon 64. The inner balloon can be sufficiently compliant to transition from a "tube" shape when not inflated to include a spheroid shape when inflated.

The irrigation balloon 64 can expand and contract through a range of circumferences during inflation and deflation. The irrigation balloon 64 can have a minimum circumference C2 when in an uninflated state (FIG. 2) having not yet been inflated during a treatment. The irrigation balloon 64 can have a maximum circumference C1 when in the inflated state (FIG. 1). The irrigation balloon 64 can be deflated to a circumference C2 sufficiently small enough to traverse vasculature, although not necessarily as small as the uninflated circumference C2. Although deflated to a circumference C2 small enough for safe extraction, the irrigation balloon 64 can retain some fluid. In embodiments where the catheter 100 is reusable, the retained fluid following treatment can be extracted from the irrigation balloon 100 after the catheter is extracted from the patient. In such instances, the irrigation balloon 100 can be collapsed to the minimum circumference C2 in the uninflated state.

The inner balloon 62 can expand and contract through a range of circumferences during inflation and deflation. The inner balloon 62 can have a minimum circumference C6 when the catheter 100 is in the uninflated state (FIG. 2) and a larger circumference C5 when the catheter 100 is in an inflated state (FIG. 1). The circumference C5 of the inner balloon 62 in the inflated state can be sized in relation to the circumference C1 of the irrigation balloon 64 in the inflated state (FIG. 1) to allow irrigation fluids to pass between the outer surface of the inner balloon 62 and the inner surface of the outer balloon 64 and through the pores 72 at a desired flow rate. When the inner balloon 62 is deflated (FIG. 3), the circumference C6 of the inner balloon 62 can return to about the same circumference C6 as when the catheter 100 is in the uninflated state (FIG. 2).

Figure 4:
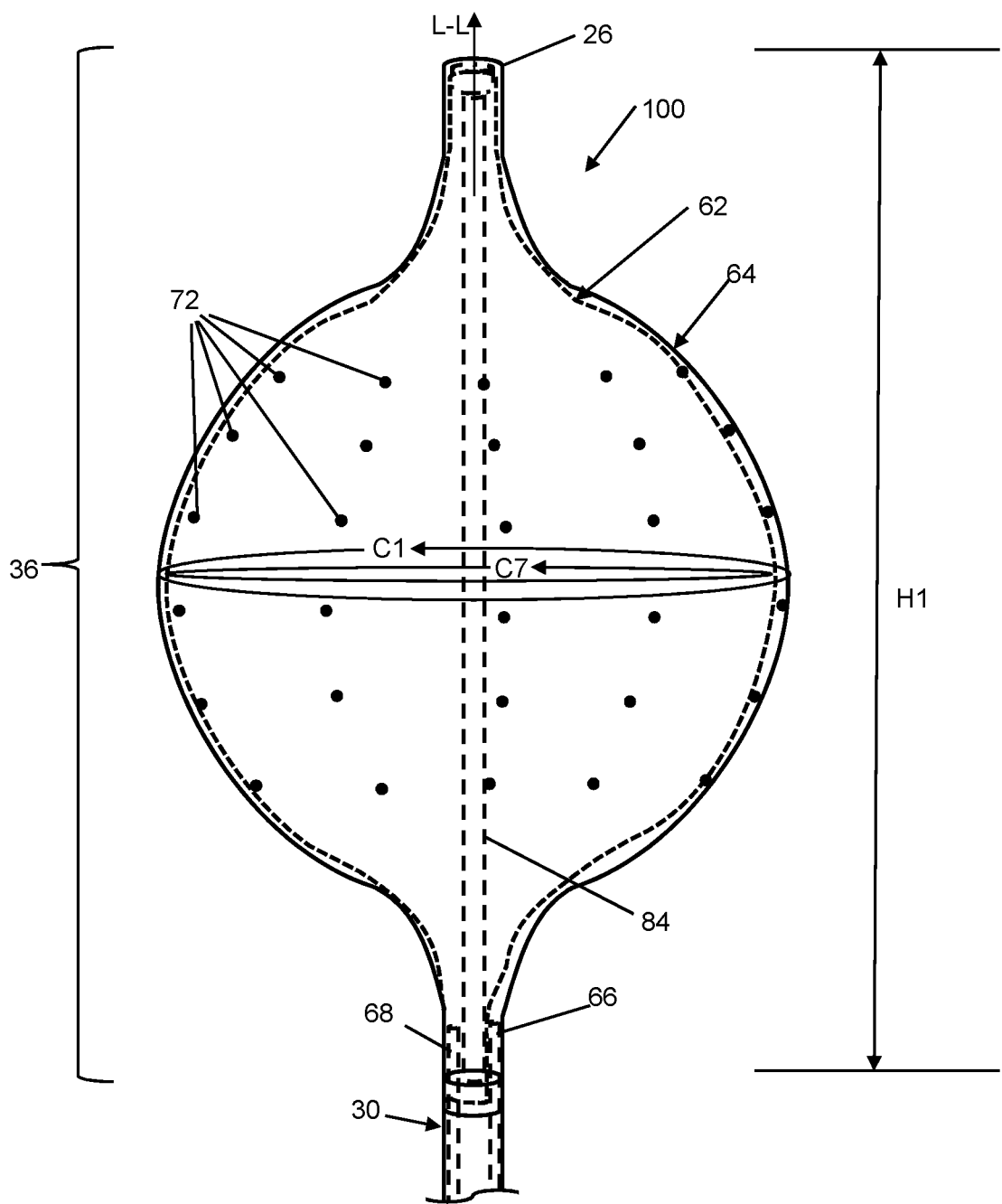
FIG. 4 is an illustration of a distal portion of a balloon-in-balloon irrigation balloon catheter in a deflation preparation state according to aspects of the present invention.

Optionally, as illustrated in FIG. 4, the inner balloon 62 can be configured to expand beyond the circumference C5 illustrated in FIG. 1. The inner balloon 62 can be sufficiently compliant to allow the inner balloon to expand to a circumference C7 greater than a circumference of inflation useful for irrigation. The expanded circumference C7 may be too large to allow irrigation fluids to pass between the outer surface of the inner balloon 62 and the inner surface of the outer balloon 64 and through pores 72 at a desired flow rate. Such functionality can be useful during deflation of the irrigation balloon 64. For instance, the irrigation balloon 64 can be deflated by first, reducing flow through the irrigation lumen 66, then expanding the volume of the inner balloon 62 from the inflated circumference for irrigation C5 to the expanded circumference C7, thereby expelling irrigation fluid through the pores 72 of the inflated irrigation balloon 64 and/or irrigation lumen 66, then the inner balloon 62 can be deflated, thereby deflating the irrigation balloon 64. In such a process, FIG. 4 illustrates the distal portion 36 of the catheter in a deflation preparation state where irrigation fluid has been expelled from the volume between the inner and irrigation balloons 62, 64.

In some applications, inflation and deflation of the inner balloon 62 can also be used to control flow rate through the pores 72 of the irrigation balloon 64. Given a non-compliant outer balloon 64, a compliant inner balloon 62 can be rapidly expanded or contracted to provide a nearly instantaneous change in flow rate through the pores 72. In some applications, during ablation, flow can be increased to decrease and regulate temperature at a treatment site; in such instances, flow can be momentarily increased solely by inflating the inner balloon 62.

The catheter can include an inner post 84. The inner post 84 can provide structural support to maintain the alignment of the distal portion 36 of the catheter 100. The inner post 84 can be concentric about the longitudinal axis L-L.

The inner post 84 can function as a telescoping shaft to allow the irrigation balloon 64 and inner balloon 62 to contract and elongate during inflation and deflation. The balloons 62, 64 can have a maximum height H2 when in an uninflated state (FIG. 2) and a minimum height H1 when inflated (FIG. 1). In some examples, the maximum height H2 can measure about 45 mm and the minimum height H1 can measure about 38 mm. Heights of about 45 mm to about 38 mm can be useful when performing procedures as illustrated and described in relation to FIGS. 6 and 7, for instance. The heights H1, H2 can otherwise be dimensioned to meet the needs of an intravascular procedure as appreciated and understood by a person of ordinary skill in the art according to the teachings of the present disclosure.

When deflated, height H3 of the balloons can be greater than the minimum height H1 and about equal to, or somewhat less than the uninflated height H2. The balloons 62, 64 can be affixed to the telescoping shaft 84 near the distal end 26 of the catheter and otherwise slidably translatable over the shaft 84. Additionally, or alternatively, the telescoping shaft can include a spring mechanism that twists and compresses in response to inflation of one or both balloons 62, 64 such as described in U.S. Pat. No. 9,907,610 to Beeckler, et. al. Alternatively, the inner post 84 need not be telescoping, in which case the balloons 62, 64 can have a substantially uniform height H1, H2, H3 when inflated and deflated through the uninflated state, inflated state, and deflated state. Regardless, of whether the shaft 84 telescopes, in some examples, the shaft 84 can optionally extend distally from the balloons 62, 64 to form a lasso catheter or focal catheter such as described in U.S. Patent Publication 2019/0298441.

Figure 5:
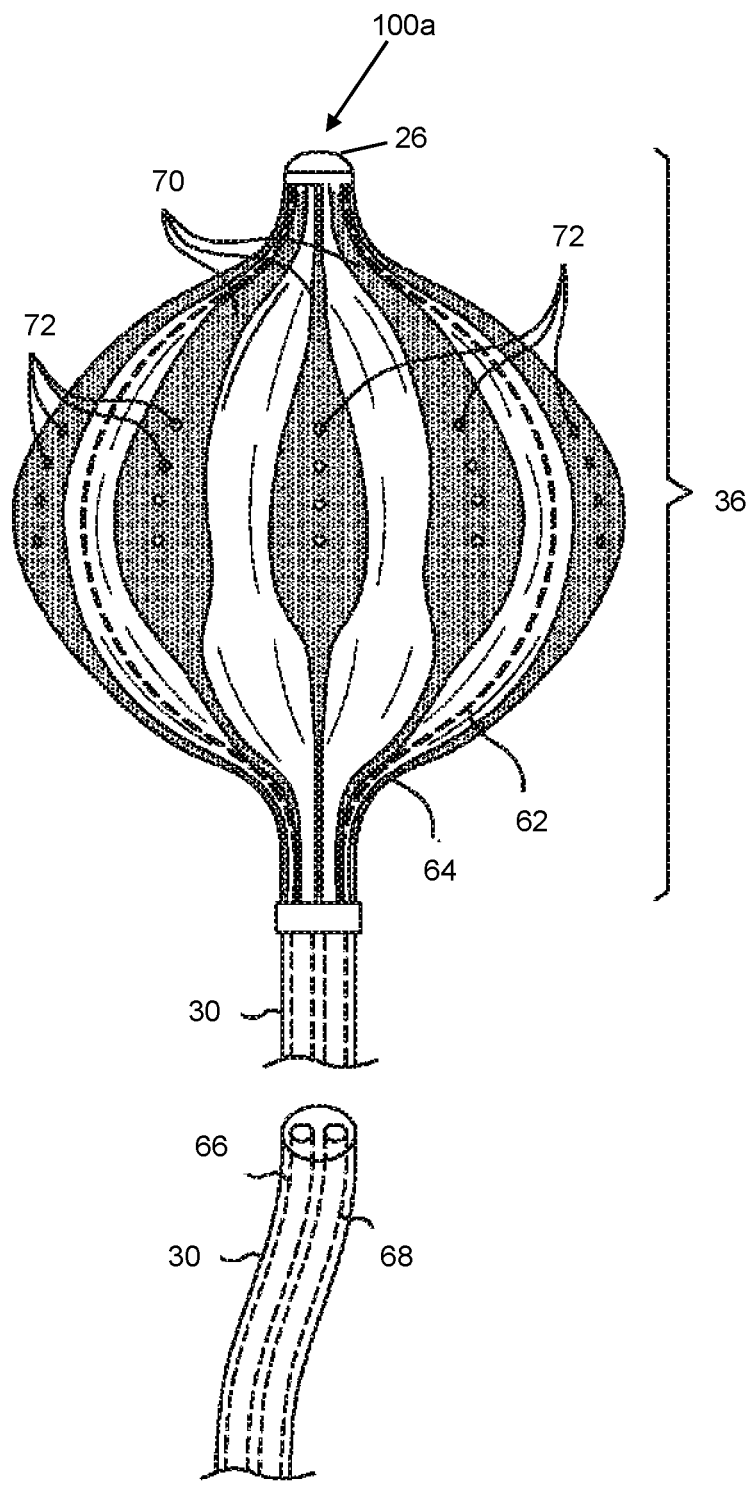
FIG. 5 is an illustration of a distal portion of a balloon-in-balloon irrigation balloon catheter having electrodes thereon according to aspects of the present invention.

FIG. 5 is an illustration of an example balloon-in-balloon irrigation balloon catheter 100a having electrodes 70 thereon. The electrodes 70 can include one or more thin metal layers formed over the outer balloon 64. Although not visible as illustrated, the distal portion 36 can include wires that convey radio-frequency energy from a console 24 (see FIG. 6) to the electrodes 70. The catheter 100 can further include thermocouples configured to sense temperature and/or position sensors configured to aid in navigation of the distal portion 36 in the patient.

The pores 72 of the irrigation balloon 64 can be positioned between the electrodes 70 to provide irrigation fluid to tissue and/or blood in a body cavity such as the heart during an ablation procedure.

Figure 6:
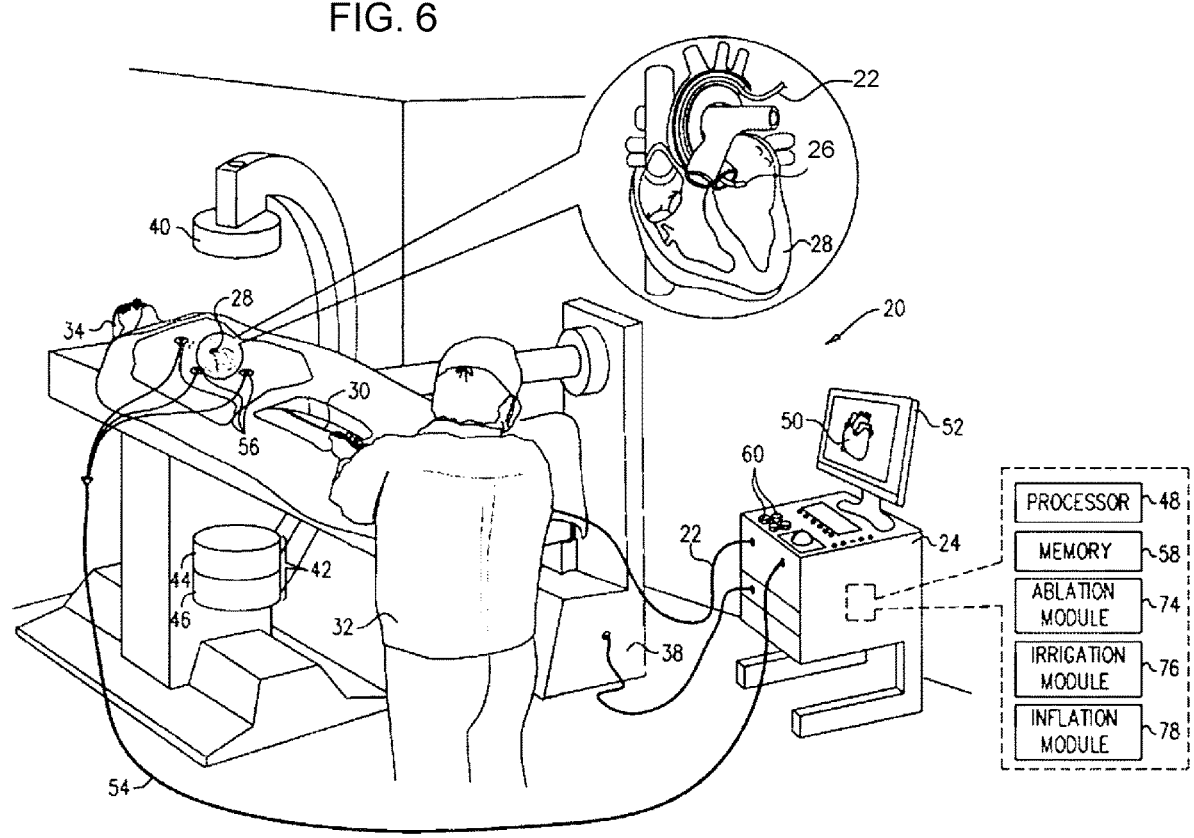
FIG. 6 is an illustration of a medical system configured to perform a medical procedure using a balloon-in-balloon irrigation balloon catheter according to aspects of the present invention.

FIG. 6 is an illustration of a medical system 20 including an irrigation balloon catheter such as the irrigation balloon catheters 100 described herein and a control console 24. The system 20 may be based, for example, on the CARTO® system, produced by Biosense Webster Inc. (Diamond Bar, Calif., U.S.A.). The system 20 may be utilized to perform medical treatments such as described herein, including performing ablation of heart tissue in a heart 28 and/or for other therapeutic and/or diagnostic purposes in the heart or in other body organs.

The catheter 100 includes an insertion tube 30, which an operator 32 inserts into a lumen, such as a chamber of heart 28, of a patient 34. As illustrated, the operator 32 may insert the insertion tube 30 through the vascular system of patient 34 so that the distal portion 36 of the catheter 100 is positioned in a chamber of the heart 28. The operator 32 can use a fluoroscopy unit 38 to visualize the distal end 26 and/or distal portion 36 inside heart 28. The fluoroscopy unit 38 can include an X-ray source 40, positioned above patient 34, which transmits X-rays through the patient. A flat panel detector 42, positioned below patient 34, can include a scintillator layer 44 which converts the X-rays which pass through patient 34 into light and a sensor layer 46 which converts the light into electrical signals.

The control console 24 can include a processor 48 that converts electrical signals from fluoroscopy unit 38 into an image 50, which the processor presents as information regarding the procedure on a display 52. The console 24 can be connected, via a cable 54, to body surface electrodes 56 that are affixed to the patient 34. The memory 58 can be in communication with the processor 48 and include instructions thereon that when executed by the processor 48 causes the processor to determine position coordinates of the distal end 26 and/or distal portion 36 of the catheter 100 inside the heart 28.

Based on the signals received from the catheter 100 and other components of system 20, the processor 48 can be configured via instructions in memory 58 to drive the display 52 to update image 50 to present a current position of the distal end 26 and/or distal portion 36 in the patient's body, as well as status information and guidance regarding the procedure that is in progress. Data representing images 50 can be stored in memory 58. The operator 32 can manipulate an image 50 using one or more input devices 60.

As illustrated, the control console 24 includes an ablation module 74, an irrigation module 76, and an internal balloon inflation tool 78 (also referred to herein as inflation module 78). In operation, the ablation module 74 monitors and controls ablation parameters such as the level and the duration of ablation power applied to ablation electrodes 70. The irrigation module 76 delivers, via irrigation conduit 66, an irrigation fluid to outer balloon 64, and monitors the flow of the irrigation fluid to the outer balloon and/or pressure of irrigation fluid in the catheter 100. The outer balloon conveys irrigation fluid to body cavity tissue via irrigation spray ports 72 (also referred to herein as pores 72). The inflation module 78 is configured to deliver, via the inflation conduit 68 (also referred to herein as inflation lumen 68), an inflation fluid to the inner balloon 62 in order to inflate the inner balloon 62. The inflation module 78 is also configured to extract the inflation fluid from the inner balloon in order to deflate the inner balloon 62.

In ablation treatments, the irrigation fluid is typically a saline solution that outer balloon delivers, via irrigation spray ports 72, to tissue in a body cavity during an ablation procedure to cool and control temperature of blood and/or tissue. The inflation fluid can include a contrast agent that can be used to enhance contrast of the inner balloon for medical imaging. For example, the contrast agent may be configured to provide radiopacity for fluoroscopy unit 38. The contrast agent can enable the console 24 to present to the operator 32, on the display 52, an image of the inner balloon 62, while the outer balloon 64 is performing an ablation procedure and conveying, via the one or more irrigation spray ports 72, irrigation fluid to tissue in the heart 28.

Figure 7:
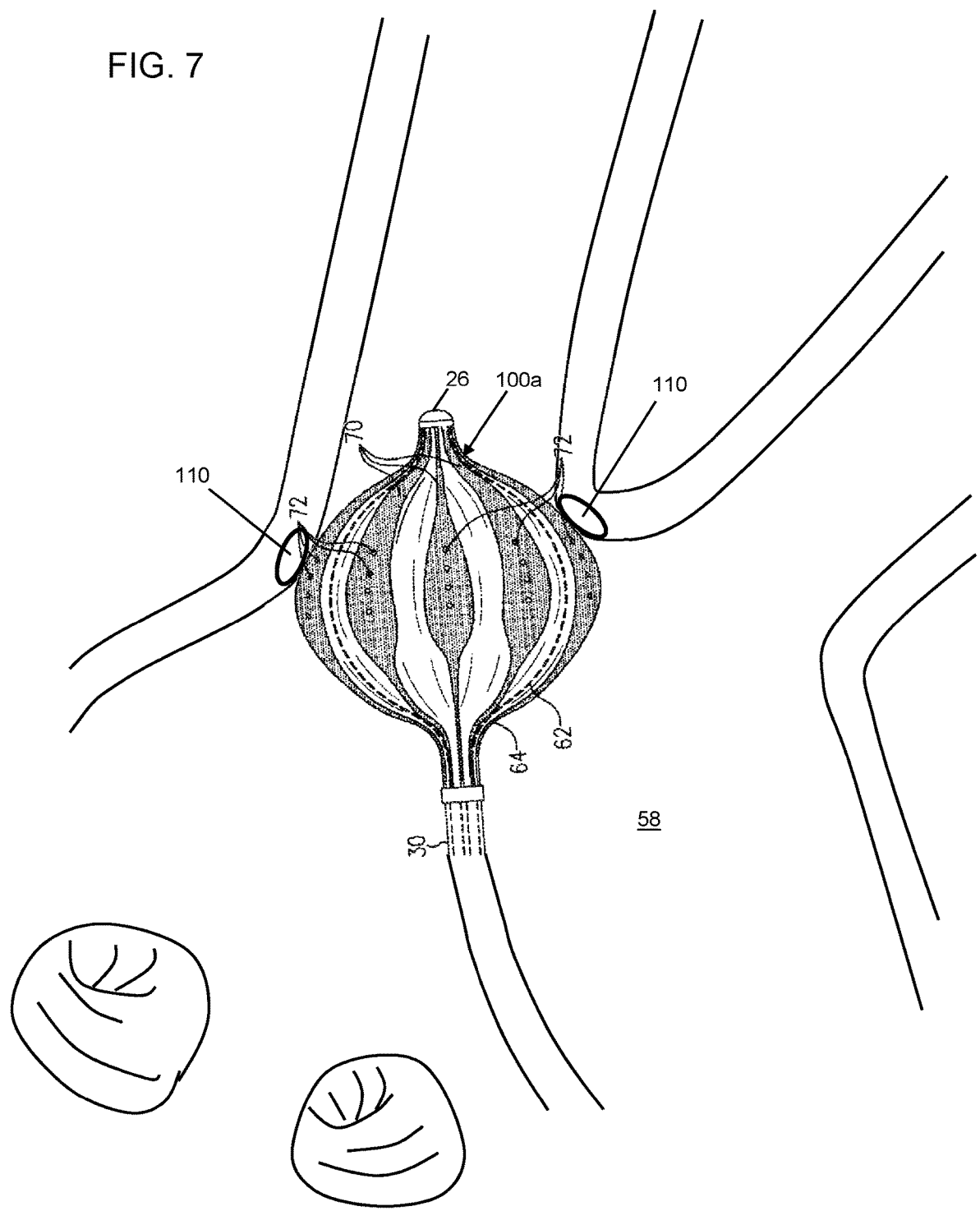
FIG. 7 is an illustration of a distal portion of a balloon-in-balloon irrigation balloon catheter in contact with endocardial tissue of the heart during an ablation procedure according to aspects of the present invention.

FIG. 7 is an illustration showing the outer balloon 64 in contact with endocardial tissue 110 of the heart 28 during an ablation procedure. The electrodes 70 are positioned to deliver electrical current to the target endocardial tissue 110 while the balloons 62, 64 are positioned to allow irrigation fluid to exit the pores 72 of the outer balloon 64 in order to regulate temperature of the target endocardial tissue 110 and adjacent area.

In some treatments, the outer balloon 64 can have an inflated shape that is constrained by the anatomy of the target tissue 110. To prevent pores 72 from becoming blocked due to contact between the inner balloon 62 and outer balloon 64 when the inflated shape of the outer balloon 64 is constrained, the inflated circumference of the inner balloon 62 can be reduced (thereby decreasing volume of the inner balloon) to increase spacing between the outer balloon 64 and inner balloon 62. The system 20 can be configured to detect blockage of the pores 72 and decrease the inflated circumference of the inner balloon 62. Detection of blockage of the pores 72 can be accomplished by comparing the flow rate of the continuous flow pump to the pressure output of the continuous flow pump; e.g. the continuous flow pump 76 can be configured to provide a feedback signal to the processor 48, and the processor 48 can be configured via instructions in memory 58 to provide a control signal to decrease pressure provided by the inflator tool 78 based on the feedback signal. Because blockage of pores 72 may generate hot spots at the treatment site, additionally, or alternatively, the processor 48 can be configured via instructions in memory 58 to receive one or more temperature signals from thermocouple(s) positioned on the irrigation balloon 64, detect hot spots based on the temperature signals, and provide a control signal to decrease pressure provided by the inflator tool 78.

In some examples, the inner balloon 62 can include a semi-compliant material such as Pebax® or high durometer polyurethane. The semi-compliant material can enable the inner balloon 62 to inflate to a predetermined shape and/or circumference. The predetermined shape can be dimensioned in relation to the outer balloon 64 to reduce the likelihood that the irrigation holes of the outer balloon 64 do not become blocked during a treatment.

Figure 8:
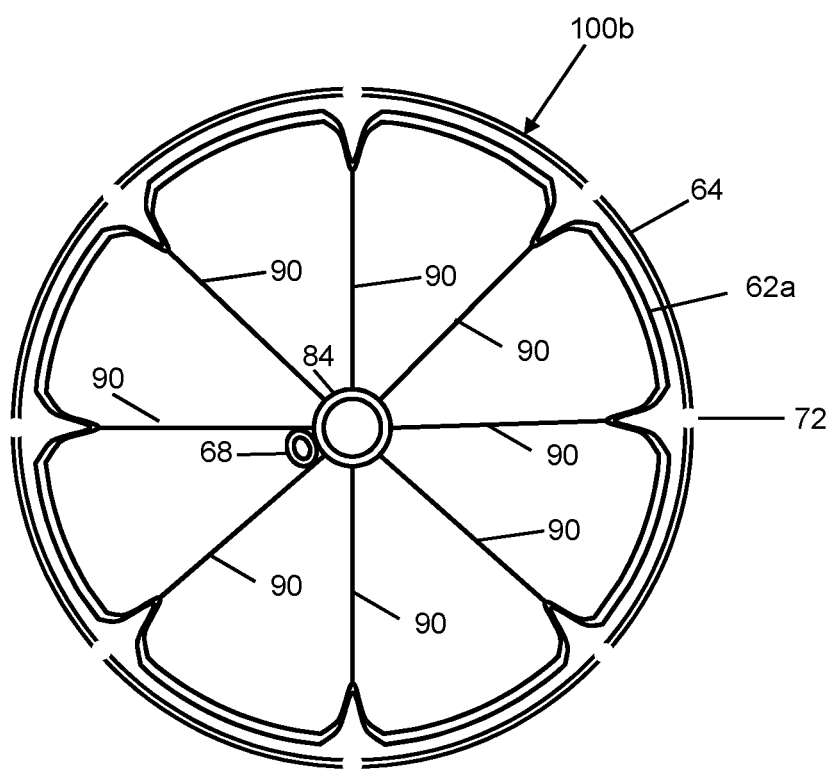
FIG. 8 is a cross-sectional illustration of a distal portion of an alternative balloon-in-balloon irrigation balloon catheter according to aspects of the present invention.

FIG. 8 is an illustration of a cross section, perpendicular to the longitudinal axis L-L of an alternative irrigation balloon catheter 100b in an inflated configuration. The alternative irrigation balloon catheter 100b includes an alternative inner balloon 62a shaped to include longitudinal internal ridges 90 aligned with the ports of the outer, irrigation balloon 64. The resulting inflated shape of the inner balloon 62 can resemble a peeled tangerine having indentations between lobes such that the indentations correspond to the ridges 90. The ridges can provide a clear pathway for irrigation fluid flow between the inner and outer balloons 62a, 64, regardless of the level of inflation of the inner balloon 62a with respect to the outer balloon 64.

Figure 9:
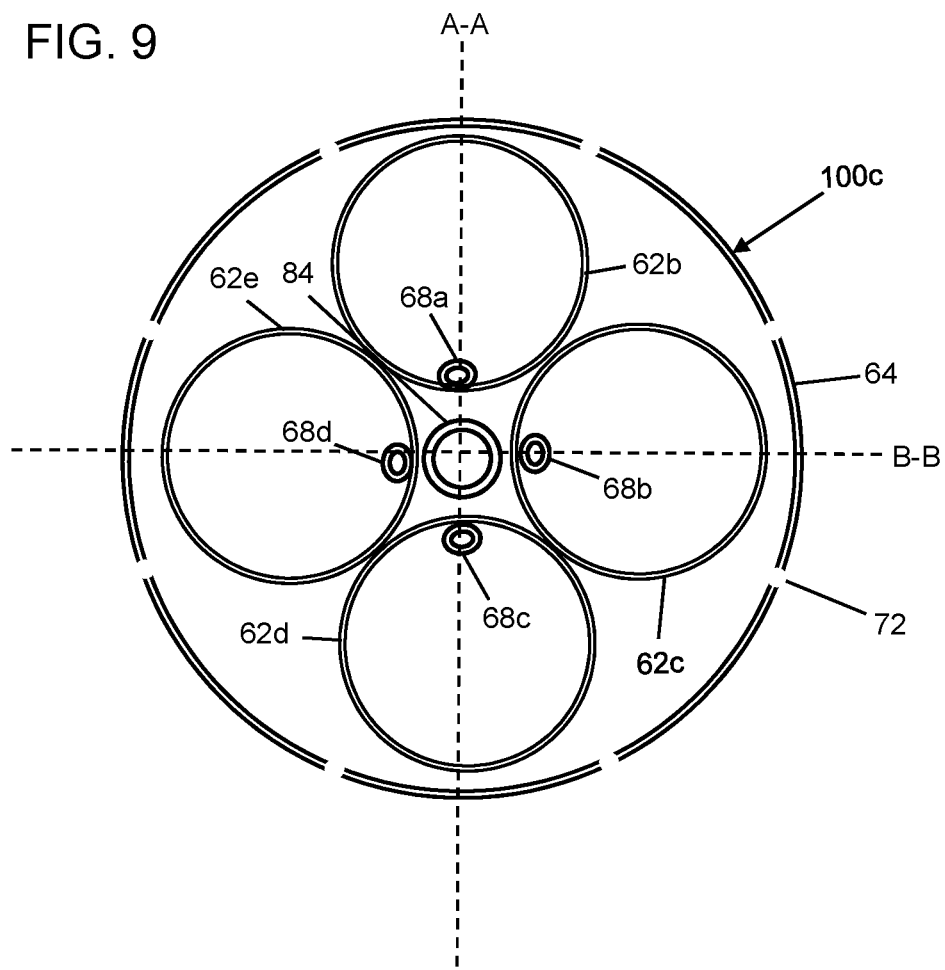
FIG. 9 is a cross-sectional illustration of a distal portion of another alternative balloon-in-balloon irrigation balloon catheter according to aspects of the present invention.

FIG. 9 is an illustration of a cross section, perpendicular to the longitudinal axis L-L of another alternative irrigation balloon catheter 100c in an inflated configuration. The alternative irrigation balloon catheter 100c includes an alternative inner balloon configuration including multiple inner balloons 62b-e. The inner balloons are arranged such that the region of each balloon closest to the outer balloon 64 is away from irrigation ports 72 so that when inflated, even if the outer balloon is deformed during a treatment such as illustrated in FIG. 7, the inner balloons 62b-e are not likely to block the irrigation ports 72 of the outer balloon 64. The catheter 100c is illustrated including four inner balloons 64b-e approximately equal in size to each other; however, the number and configuration of inner balloons can be adjusted based on position of irrigation ports 72 and likely deformation of the outer balloon 64 during treatment as appreciated and understood by a person of ordinary skill in the art according to the teachings of the present disclosure. When inflated, each of the inner balloons 64b-e can form a lobe that is elongated in the direction of the longitudinal axis L-L such that the inner balloons 64b-e fill from about 70% to about 90% of the volume of the outer balloon 64.

Each of the inner balloons 62-e can be separately inflatable via a respective inflation conduit 68a-d. In some applications, individual inflation/deflation of inner balloons 62b-e can be used to selectively apply electrodes to tissue at a treatment site. For instance, a first pair of opposite balloons 62b, 62d aligned on a first axis A-A can each be respectively inflated to a greater circumference than a second pair of opposite balloons 62c, 62e aligned on a second axis B-B to cause the outer balloon 64 to take on an oblong shape cross-section shape that is wider along the first axis A-A and narrower along the second axis B-B. In some applications, the oblong shape can serve to move ablation electrodes near the first axis A-A closer to tissue with moving ablation electrodes near the second axis B-B away from tissue.

Figure 10:
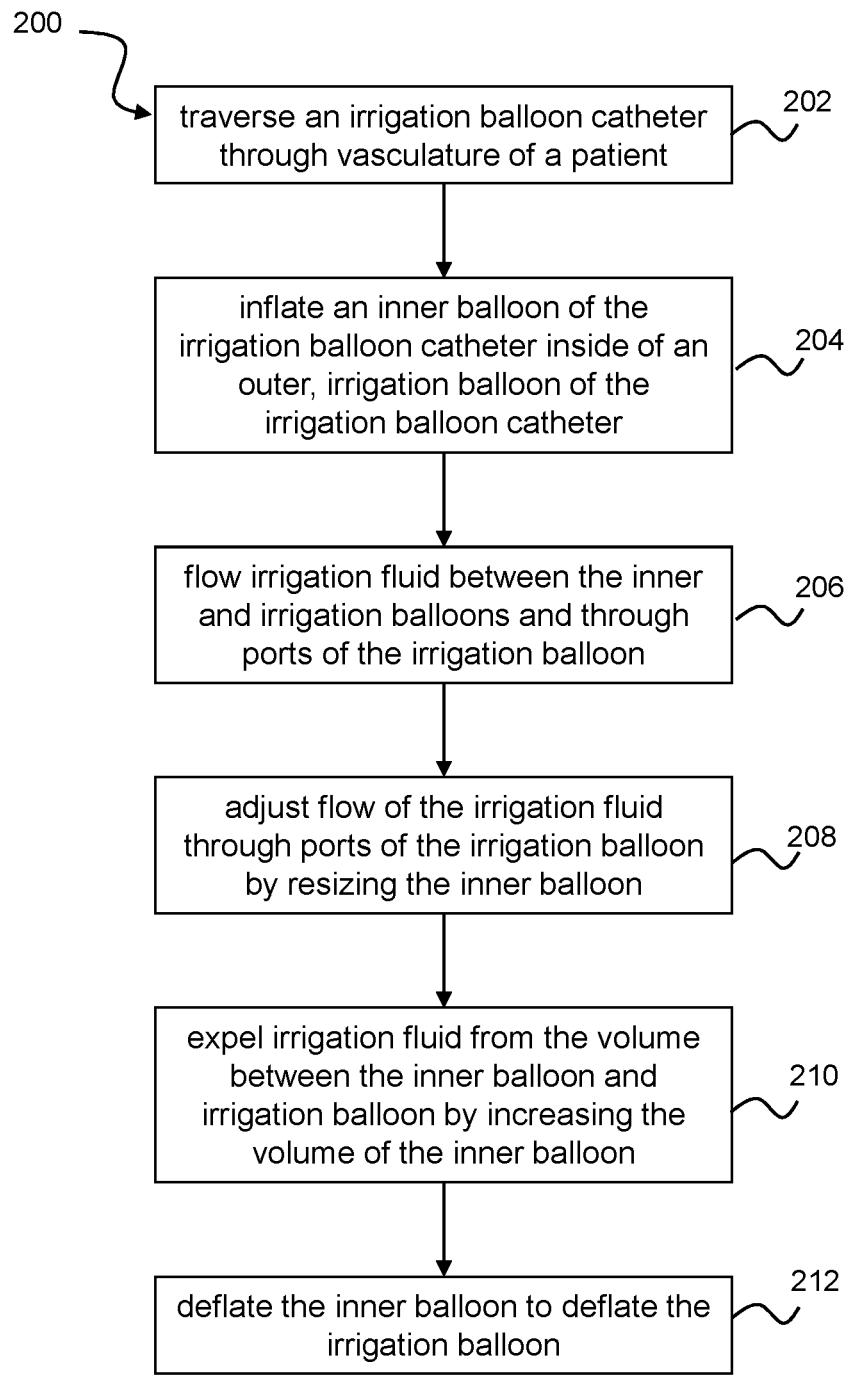
FIG. 10 is a flow diagram of a method of treatment according to aspects of the present invention

FIG. 10 is a flow diagram illustrating steps of a method 200 of treatment. A successful treatment procedure need not include every step illustrated. Further, certain steps can be performed in an alternative order as appreciated and understood by a person or ordinary skill in the art according to the teachings of the present disclosure. Additional steps can be performed in combination of some or all of the steps illustrated in the method 200.

At step 202, an irrigation balloon catheter having an inner balloon and irrigation balloon can be traversed through vasculature of patient. The irrigation balloon catheter can be an irrigation balloon catheter 100, 100a, 100b illustrated and/or described herein, a variation thereof, or alternative thereto as appreciated and understood by a person of ordinary skill in the art according to the teachings of this disclosure.

At step 204, the inner balloon of the irrigation balloon catheter traversed in step 202 can be inflated inside of the irrigation balloon. The inner balloon and irrigation balloon can be any combination of inner balloon and irrigation balloon 62, 62a, 64 illustrated and/or described herein, a variation thereof, or alternative thereto as appreciated and understood by a person of ordinary skill in the art according to the teachings of this disclosure. In some examples, the inner balloon can be inflated for the purpose of expediting inflation of the irrigation balloon.

At step 206, irrigation fluid can be flowed through a volume defined by an inner surface of the irrigation balloon and an outer surface of the inner balloon and through pores of the irrigation balloon. The irrigation fluid can follow flow paths illustrated and/or described herein, a variation thereof, or alternative thereto as appreciated and understood by a person of ordinary skill in the art according to the teachings of this disclosure.

At step 208, flow of the irrigation fluid through one or more of the pores of the irrigation balloon can be adjusted by resizing the inner balloon. The inner balloon can be resized to a larger or smaller volume and/or circumference. Flow of the irrigation fluid can be increased or decreased as a result of the resizing of the inner balloon. The inner balloon can be resized as illustrated and/or described herein, or via alternative methods as appreciated and understood by a person of ordinary skill in the art according to the teachings of this disclosure. In some examples, the volume of the inner balloon can be decreased in response to detecting blockage of pores of the irrigation balloon.

At step 210, irrigation fluid from the volume defined by the inner surface of the irrigation balloon and the outer surface of the inner balloon can be expelled by increasing the volume of the inner balloon. In some examples, the volume of the inner balloon can be increased beyond a preferred or effective volume for irrigation during an ablation procedure.

At step 212, the inner balloon can be deflated. In some examples including step 210, the inner balloon can be deflated immediately after expelling irrigation fluid from the volume defined by the inner surface of the irrigation balloon and the outer surface of the inner balloon. In some examples, the volume of the inner balloon can be decreased while flowing irrigation fluid through the volume defined by the inner surface of the irrigation balloon and the outer surface of the inner balloon and through pores of the irrigation balloon so that the irrigation balloon is rapidly deflated by the rapid decrease in the volume of the inner balloon. In some examples, the volume of the irrigation balloon can be decreased solely by decreasing the volume of the inner balloon.

The descriptions contained herein are examples of embodiments of the invention and are not intended in any way to limit the scope of the invention. As described herein, the invention contemplates many variations and modifications of an irrigation balloon catheter including alternative materials for component parts, alternative geometrical configurations, alternative methods of construction, alternative methods of use, additional or alternative films adhered to the outer balloon, additional sensor structures positioned approximate the distal end of the catheter, and additional or alternative structures inside of the inner balloon to structurally support the dual balloons. Modifications and variations apparent to those having ordinary skill in the art according to the teachings of this disclosure are intended to be within the scope of the claims which follow.

What is claimed is:

1. An irrigation balloon catheter system comprising:
a tubular body sized to traverse vasculature of a patient;
an irrigation balloon comprising pores therethrough, the irrigation balloon inflatable to comprise a first inflated shape that is circularly symmetrical about a longitudinal axis when the irrigation balloon is unconstrained;
an inner balloon positioned within the irrigation balloon, the inner balloon inflatable to comprise a second inflated shape that is circularly symmetrical about the longitudinal axis and separated from the first inflated shape of the irrigation balloon at least in the vicinity of the pores;
an irrigation lumen in communication with the irrigation balloon and extending along the tubular body;
an inflation lumen in communication with the inner balloon and extending along the tubular body so that deflation of the inner balloon causes a rapid deflation of the irrigation balloon;
an inflator tool in communication with the inner balloon via the inflation lumen, the inflator tool configured to provide a first fluid at a predetermined pressure;
one or more thermocouples disposed on the irrigation balloon;
a processor; and
computer readable medium in communication with the processor, the computer readable medium comprising instructions thereon that when executed by the processor cause the processor to:
receive one or more signals from the one or more thermocouples, and
provide, in response to receiving the one or more signals from the one or more thermocouples, a command signal to the inflator tool to cause the inflator tool to decrease pressure of the first fluid.

2. The irrigation catheter system of claim 1,
the irrigation balloon being affixed to the inner balloon at first and second balloon ends,
the first inflated shape being circularly symmetrical about the longitudinal axis from the first balloon end to the second balloon end, and
the second inflated shape being circularly symmetrical about the longitudinal axis from the first balloon end to the second balloon end.

3. The irrigation balloon catheter system of claim 1,
the pores defining one or more planes perpendicular to the longitudinal axis, and
the second inflated shape comprising a circular cross section in each of the one or more planes.

4. The irrigation balloon catheter system of claim 1, the irrigation lumen and inflation lumen being isolated from each other.

5. The irrigation balloon catheter system of claim 1,
the irrigation balloon comprising a non-compliant membrane, and
the inner balloon comprising a compliant membrane.

6. The irrigation balloon catheter system of claim 1, the pores being sized to allow saline solution to pass therethrough.

7. The irrigation balloon catheter system of claim 1, the second inflated shape comprising a volume that is about 80% to about 90% of a volume of the first inflated shape.

8. The irrigation balloon catheter system of claim 1, the inner balloon comprising a fluid impermeable membrane.

9. A system comprising:
an irrigation balloon catheter comprising:
a tubular body sized to traverse vasculature of a patient,
an irrigation balloon comprising pores therethrough, the irrigation balloon inflatable to comprise a first inflated shape that is circularly symmetrical about a longitudinal axis when the irrigation balloon is unconstrained,
an inner balloon positioned within the irrigation balloon, the inner balloon inflatable to comprise a second inflated shape that is circularly symmetrical about the longitudinal axis and separated from the first inflated shape of the irrigation balloon at least in the vicinity of the pores,
an irrigation lumen in communication with the irrigation balloon and extending along the tubular body, and
an inflation lumen in communication with the inner balloon and extending along the tubular body;
a continuous flow pump in communication with the irrigation balloon via the irrigation lumen;
an inflator tool in communication with the inner balloon via the inflation lumen, the inflator tool configured to provide a first fluid at a predetermined pressure;
one or more thermocouples disposed on the irrigation balloon;
a processor; and
computer readable medium in communication with the processor, the computer readable medium comprising instructions thereon that when executed by the processor cause the processor to:
receive one or more signals from the one or more thermocouples, and
provide, in response to receiving the one or more signals from the one or more thermocouples, a command signal to the inflator tool to cause the inflator tool to decrease pressure of the first fluid.

10. The system of claim 9, the computer readable medium further comprising instructions thereon that when executed by the processor cause the processor to:
provide a command signal to the inflator tool to cause the inflator tool to provide the first fluid at the predetermined pressure, and
provide a command signal to the continuous flow pump to cause the continuous flow pump to pump a second fluid at a predetermined flow rate.

11. The system of claim 9, the computer readable medium further comprising instructions thereon that when executed by the processor cause the processor to:
receive a feedback signal from the continuous flow pump, and
provide, in response to receiving the feedback signal, a command signal to the inflator tool to cause the inflator tool to decrease pressure of the first fluid.

12. A method of treatment comprising:
traversing an irrigation balloon catheter comprising an inner balloon and irrigation balloon through vasculature of patient;
inflating the inner balloon inside of the irrigation balloon;
flowing irrigation fluid through a volume defined by an inner surface of the irrigation balloon and an outer surface of the inner balloon and through pores of the irrigation balloon;
adjusting flow of the irrigation fluid through one or more of the pores of the irrigation balloon by resizing the inner balloon;
detecting blockage of some or all of the one or more pores; and
decreasing the volume of the inner balloon in response to detecting blockage of some or all of the one or more pores.

13. The method of claim 12 further comprising:
expelling irrigation fluid form the volume defined by the inner surface of the irrigation balloon and the outer surface of the inner balloon by increasing the volume of the inner balloon.

14. The method of claim 13, further comprising:
deflating the inner balloon immediately after expelling irrigation fluid from the volume defined by the inner surface of the irrigation balloon and the outer surface of the inner balloon.

15. The method of claim 12, further comprising:
decreasing the volume of the inner balloon while flowing irrigation fluid through the volume defined by the inner surface of the irrigation balloon and the outer surface of the inner balloon and through pores of the irrigation balloon so that the irrigation balloon is rapidly deflated by the decrease in the volume of the inner balloon.

16. The method of claim 12, further comprising:
decreasing the volume of the irrigation balloon solely by decreasing the volume of the inner balloon.

17. A method of treatment comprising:
traversing an irrigation balloon catheter comprising an inner balloon and irrigation balloon through vasculature of the patient;
inflating the inner balloon inside of the irrigation balloon;
flowing irrigation fluid through a volume defined by an inner surface of the irrigation balloon and an outer surface of the inner balloon and through pores of the irrigation balloon;
expelling irrigation fluid from the volume defined by the inner surface of the irrigation balloon and the outer surface of the inner balloon by increasing the volume of the inner balloon;
detecting blockage of some or all of the one or more pores; and
decreasing the volume of the inner balloon in response to detecting blockage of some or all of the one or more pores.

18. The method of claim 17, further comprising:
deflating the inner balloon immediately after expelling irrigation fluid from the volume defined by the inner surface of the irrigation balloon and the outer surface of the inner balloon.

19. An irrigation balloon catheter system comprising:
a tubular body sized to traverse vasculature of a patient;
an irrigation balloon comprising pores therethrough, the irrigation balloon inflatable to comprise a first inflated shape that is circularly symmetrical about a longitudinal axis when the irrigation balloon is unconstrained;
an inner balloon positioned within the irrigation balloon, the inner balloon inflatable to comprise a second inflated shape comprising longitudinal ridges aligned with the pores of the irrigation balloon and separating an outer surface of the inner balloon from an inner surface of the irrigation balloon in the vicinity of the pores;
an irrigation lumen in communication with the irrigation balloon and extending along the tubular body;
an inflation lumen in communication with the inner balloon and extending along the tubular body so that deflation of the inner balloon causes a rapid deflation of the irrigation balloon;
an inflator tool in communication with the inner balloon via the inflation lumen configured to provide a first fluid at a predetermined pressure;
a continuous flow pump in communication with the irrigation balloon via the irrigation lumen;
a processor; and
computer readable medium in communication with the processor, the computer readable medium comprising instructions thereon that when executed by the processor cause the processor to:
receive a signal from the continuous flow pump indicative of a blockage of some or all of the pores; and
provide a command signal to the inflator tool to cause the inflator tool to decrease pressure of the first fluid.

20. An irrigation balloon catheter system comprising:
a tubular body sized to traverse vasculature of a patient;
an irrigation balloon comprising pores therethrough;
a plurality of inner balloons inflatable within the irrigation balloon;
an irrigation lumen in communication with the irrigation balloon and extending along the tubular body;
a plurality of inflation lumens each in communication with a respective inner balloon of the plurality of inner balloons and extending along the tubular body
an inflator tool in communication with plurality of inner balloons via the plurality of inflation lumens, the inflator tool configured to provide a first fluid at a predetermined pressure;
a continuous flow pump in communication with the irrigation balloon via the irrigation lumen;
a processor; and computer readable medium in communication with the processor, the computer readable medium comprising instructions thereon that when executed by the processor cause the processor to:

receive a signal from the continuous flow pump indicative of a blockage of some or all of the pores; and provide a command signal to the inflator tool to cause the inflator tool to decrease pressure of the first fluid.

* * * * *